United States Patent [19]

Peters et al.

[11] Patent Number: 4,712,549
[45] Date of Patent: Dec. 15, 1987

[54] AUTOMATIC HEMOSTATIC CLIP APPLIER

[75] Inventors: Rudolph Peters; Ronald Peters; William Taylor, all of Oakland, Calif.

[73] Assignee: Edward Weck & Co., Research Triangle Park, N.C.

[21] Appl. No.: 750,158

[22] Filed: Jul. 1, 1985

[51] Int. Cl.⁴ .............................................. A61B 17/12
[52] U.S. Cl. .................................. 128/325; 29/243.56; 72/410; 227/DIG. 1
[58] Field of Search .............................. 128/325, 326; 29/243.56; 72/410; 227/DIG. 1 R, DIG. 1 S, DIG. 1 C

[56] References Cited

U.S. PATENT DOCUMENTS

| | | | |
|---|---|---|---|
| 4,325,376 | 4/1982 | Klieman et al. | 128/325 |
| 4,412,539 | 11/1983 | Jarvik | 128/325 |
| 4,430,997 | 2/1984 | DiGiovanni et al. | 128/325 X |
| 4,448,193 | 5/1984 | Ivanov | 128/326 |
| 4,450,839 | 5/1984 | Transue | 128/325 |
| 4,452,376 | 6/1984 | Klieman et al. | 128/325 X |
| 4,509,518 | 4/1985 | McGarry et al. | 128/325 |
| 4,522,207 | 6/1985 | Klieman et al. | 128/326 X |
| 4,534,351 | 8/1985 | Rothfuss et al. | 128/325 X |

*Primary Examiner*—Albert J. Makay
*Assistant Examiner*—Steven E. Warner
*Attorney, Agent, or Firm*—Harris Zimmerman; Howard Cohen

[57] ABSTRACT

A tool for storing dispensing, and applying hemostatic clips includes a shell-like housing, and a pair of ring-handle actuating levers extending therefrom. An elongated dispensing and applying portion extends longitudinally from the housing, and includes a jaw strut extending fixedly from the housing with a pair of laterally opposed jaw members pivotally supported on a distal portion thereof. A channel-like jaw housing extends from the housing in longitudinally translatable fashion, and is received about the jaw strut and jaw members. A magazine member secured to the jaw strut stores a plurality of hemostatic clips in serial, end to end fashion, and is disposed to deliver the distal-most clip between the open jaw members. A feeder slide adjacent to the jaw strut is resiliently biased to urge the clip toward the distal end of the jaw members. Within the housing a shuttle block is disposed for longitudinal translation by squeezing of the levers. A flexible band extends from the shuttle block, about a pulley on the jaw housing, to the feeder slide. As the shuttle is urged distally, the band pulls the feeder slide proximately to clear the jaw members. At the limit of travel of the slide, the band tension on the pulley then drives the jaw housing distally to translate about the jaw members, closing the jaws and crimping the clip completely flat. The shuttle also decrements a counter wheel to show the number of clips remaining in the tool.

24 Claims, 16 Drawing Figures

FIG_6

FIG_5

FIG_4

AUTOMATIC HEMOSTATIC CLIP APPLIER

BACKGROUND OF THE INVENTION

In the past several years hemostatic clips have been introduced to supplant prior art suturing techniques for the purpose of tying off bleeding blood vessels in surgery and traumatic medical care. The clips are applied by any of a plethora of tools known in the prior art. Generally, the tool includes opposed jaws which crimp the U-shaped clip flat, blocking the lumen of the blood vessel engaged between the opposed legs of the clip.

It is usually advantageous to provide a plurality of clips in the tool, and to feed them serially to the jaws, thus saving the time of the surgical team in applying the clips singularly. Given such a tool, it should be possible to greatly hasten and facilitate an important and necessary part of virtually every surgical procedure.

However, deficiencies in prior art tools have limited the usefulness and acceptance of hemostatic clips in surgery and trauma care. Many of the simpler applicator tools do not crimp the clip completely flat, so that all bleeding is not stopped. Furthermore, the clip feed mechanisms are often unwieldy, requiring manual contortions which are difficult and tiresome to the user. Also, the manual motion required to dispense and crimp the clip often causes erratic motion of the tool, especially at the delivery end, so that placement of the clip can only be approximate. In many surgical procedures, this factor is unacceptable.

There are more substantial tools known in the prior art which overcome the difficulties enumerated above. One such exemplary tool is described in copending U.S. patent application Ser. No. 237,465, filed Feb. 23, 1981 by the present inventors. Such a tool, however, is relatively expensive compared to the cost of the hemostatic clips which are typically used in a single surgical procedure. Also, the tool must be sterilized and reloaded after each use. Thus, there is a disincentive for hospitals and physicians to purchase such a tool. Clearly there is a need in the art for a simple tool, inexpensive to manufacture and sell, which easily and accurately dispenses and crimps a number of hemostatic clips.

SUMMARY OF THE PRESENT INVENTION

The present invention generally comprises a tool for storing, dispensing, and crimping completely a number of hemostatic clips for surgical and medical purposes. A significant aspect of the tool is that it achieves reliable and accurate dispensing and placement of the clips, while employing a simple mechanism having few parts. Thus the invention can be manufactured inexpensively, and can be cost-effectively disposed after use. Thus the labor and cost of resterilizing and reloading the tool is eliminated. Other features of the tool include a counter for clearly indicating the number of hemostatic clips remaining in the tool magazine, and an actuating mechanism which permits full visualization of the clip being dispensed and crimped, as well as steady and accurate positioning of the jaws as the mechanism is operated.

The tool for storing dispensing, and applying hemostatic clips includes a shell-like housing, and a pair of ring-handle actuating levers extending from opposite sides thereof. An elongated dispensing and applying portion extends longitudinally from the housing, and includes a jaw strut extending fixedly from the housing with a pair of laterally opposed jaw members pivotally supported on a distal portion thereof. Thus the jaws themselves are secured at a fixed, invariant length from the housing and the actuating levers.

A channel-like jaw housing extends from the housing in longitudinally translatable fashion, and is received about the jaw strut and jaw members. The jaw members include outer, laterally opposed camming surfaces, so that distal translation of the jaw housing engages the camming surfaces and drives the jaw members together to crimp a hemostatic clip therebetween. A magazine assembly is secured to the jaw strut to store a plurality of hemostatic clips in serial, end to end column fashion, with an elastic band urging the column distally to deliver the distal-most clip between the open jaw members. A feeder slide adjacent to the jaw strut and within the jaw housing channel is resiliently biased to urge the delivered clip toward the distal end of the jaw members.

Within the housing a shuttle block is disposed for longitudinal translation in a track therein. The actuating levers are pivotally joined to the housing, with a dogleg portion of each lever engaging the shuttle block so that manually squeezing the levers together drives the shuttle block to translate distally in its track. A flexible band extends in a U-configuration from the shuttle block, about a pulley on the jaw housing, to the feeder slide. As the shuttle is urged distally, the band pulls the feeder slide proximally to clear the jaw members. At the limit of travel of the slide, the band tension on the pulley then drives the jaw housing distally to translate about the jaw members, closing the jaws and crimping the clip completely flat. The shuttle also includes an arm which decrements a counter wheel in ratchet fashion to show the number of clips remaining in the magazine.

When the levers are released, spring force initially urges the jaw housing proximally, permitting the jaws to open and to receive a new clip from the magazine. The feeder slide is then urged by spring force to translate distally between the opened jaw members, driving the new clip to the ends of the jaws and positioning the new clip for the next crimping cycle.

DESCRIPTION OF THE PREFERRED EMBODIMENT

The present invention generally comprises a tool which is adapted to store a plurality of hemostatic clips, and to dispense and crimp the clips serially, singly, and completely. A salient feature of the tool is that it is designed to provide smooth operation and accurate placement of the clips using the natural and comfortable manual flexure of one hand, while it employs a small number of parts involved in a simple yet elegant and effective mechanism. Because of these qualities, the tool may be made inexpensively, and can be sold in sterilized packs for a single use, and then be discarded.

Figures 1, 3:
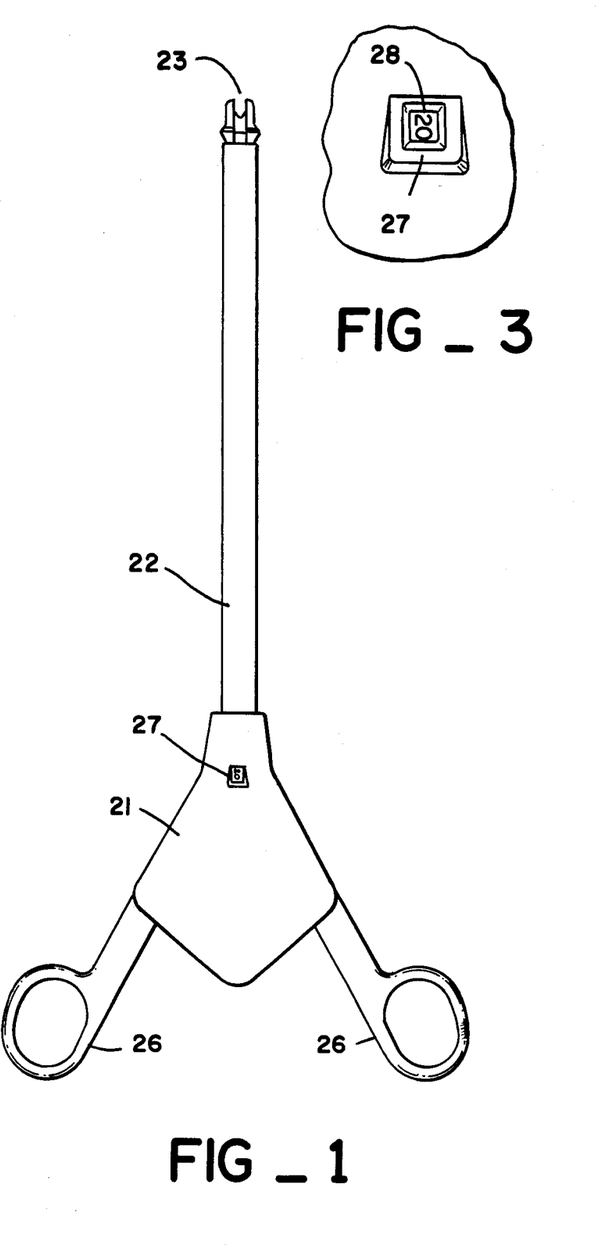
FIG. 1 is a plan view of the tool of the present invention for storing, dispensing, and applying hemostatic clips.
FIG. 3 is an enlarged detailed view of the indicator window of the tool of the present invention.
Figure 2:
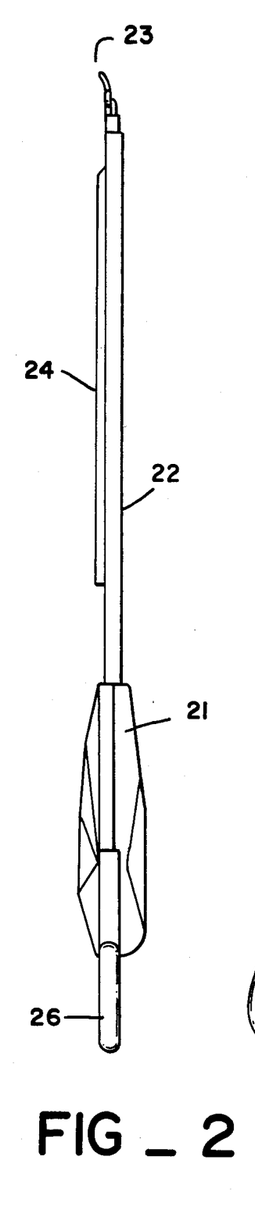
FIG. 2 is a side view of the tool as shown in FIG. 1.

With reference to FIGS. 1 and 2, the major components of the tool include a housing portion 21 having an irregular, rhomboidal configuration, and an elongated dispensing and crimping portion 22 extending longitudinally therefrom. A jaw assembly 23 at the distal end of the portion 22 is adapted to dispense and crimp each of a plurality of hemostatic clips. It should be noted that the jaw assembly curves from the longitudinal axis of the portion 22, so that the surgeon or other user easily may visualize the clip being applied. A magazine assembly 24 is joined fixedly to the portion 22, and is adapted to retain the plurality of hemostatic clips and to feed them serially to the jaw assembly 23, as will be explained in the following description. A pair of ring-handle actuating levers 26 extend from the housing 21 in linked pivotting fashion, so that the levers must be squeezed together through mutually equal angles to operate the tool. As a result, the angle of each of the levers with respect to the longitudinal axis is the same, resulting in accurate placement and easy control of the jaw portion at the distal end of the portion 22.

The housing 21 is also provided with an indicator window 27 formed in the top portion of the housing, and shown in detail in FIG. 3. An indicia display 28 is presented in the window to indicate the exact number of clips remaining in the magazine assembly 24 of the tool. Thus the user is always apprised of the number of remaining clips, and can plan the hemostatic clip requirements with certain knowledge.

Figure 5:
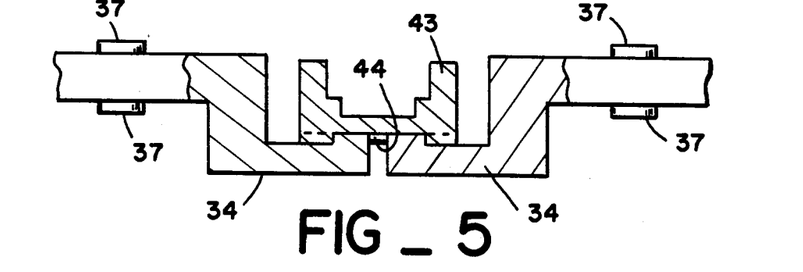
FIG. 5 is a further cross-sectional elevation taken through the shuttle and handle assembly of the tool.
Figure 6:
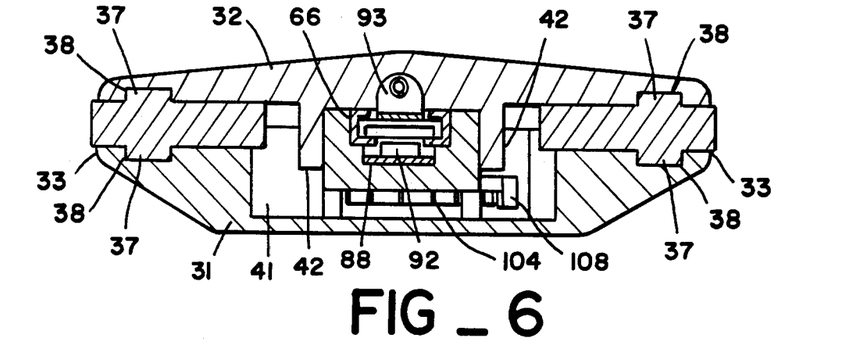
FIG. 6 is a cross-sectional elevation taken through the housing, shuttle block assembly, and handle assembly of the tool of the present invention.
Figure 9:
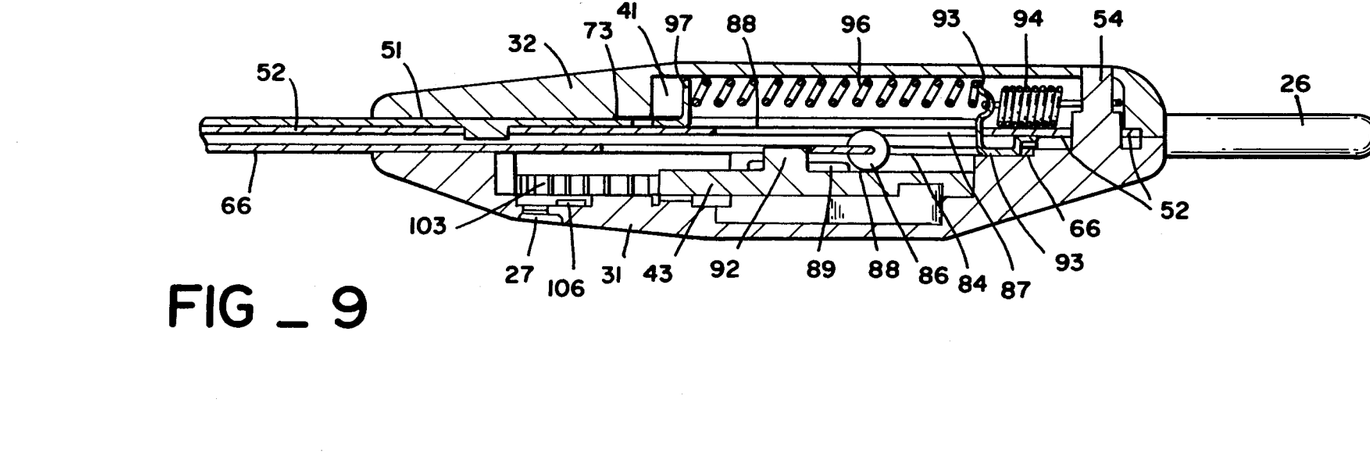
FIG. 9 is a cross-sectional side view of the housing and actuating mechanism of the tool.

With reference to FIGS. 6 and 9, the housing 21 is comprised of top and bottom members 31 and 32 having approximately the same outer plan configuration and joined together by screws or the like (not shown). The members 31 and 32 form a generally hollow, shell-like housing structure. The housing members together define laterally opposed side openings 33 disposed generally at the vertices of the rhomboidal configuration. The distal ends of the handle levers 26 are provided with dogleg portions 34 extending inwardly each toward the other and received within the housing. The junctures of the dogleg portions 34 with their respective external lever members 36 are each provided with a pair of pivot knobs 37 extending from opposed top and bottom surfaces of the junction portion. The knobs 37 are rotatably received in suitably formed, aligned recesses 38 in the top and bottom housing members 31 and 32, so that the levers are freely pivotally supported by the housing assembly. With the levers 26 in the quiescent, extended position, the inner ends of the dogleg portions 34 are disposed in closely adjacent opposition, as shown in FIG. 5.

With regard to FIG. 6 in particular, the interior chamber 41 of the housing 21 is provided with interior wall segments 42 extending generally longitudinally and defining, together with other interior surfaces, a channel-like track extending longitudinally in the chamber 41. A shuttle block 43 is disposed within the chamber 41 and configured to be received in the track therein in slidable, freely translating fashion. As shown in FIGS. 4–6, 9, 15, and 16, the shuttle block comprises an irregularly shaped, generally rectangular member having upright surfaces which engage the wall segments 42, as well as other interior surfaces, to constrain movement of the shuttle block to longitudinal translation in the interior track.

Figure 4:
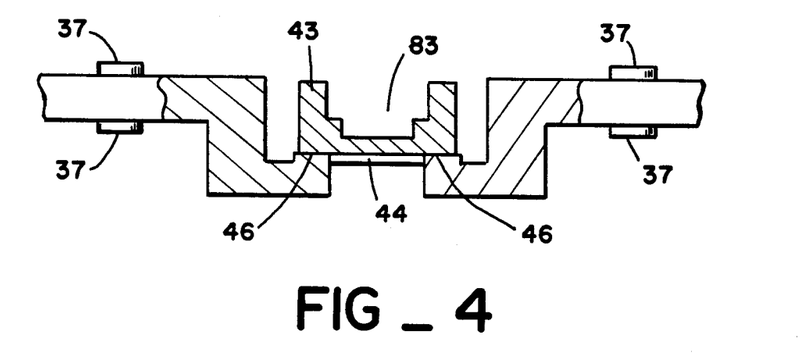
FIG. 4 is a cross-sectional elevation taken through the shuttle block and handle portion of the tool of the present invention.
Figure 7:
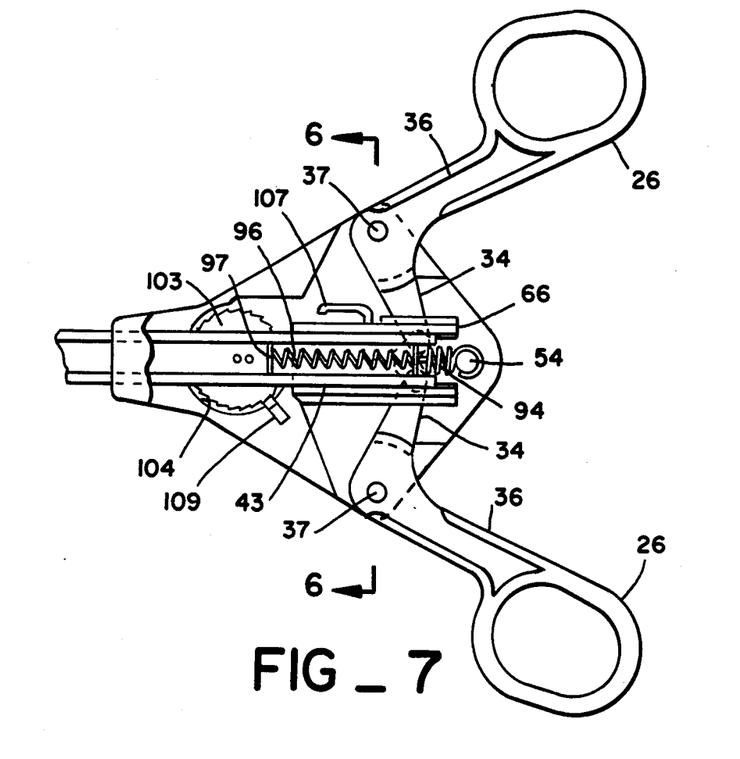
FIG. 7 is an enlarged plan view of the actuating mechanism within the housing of the tool, showing the handles and mechanism in the quiescent position.
Figure 8:
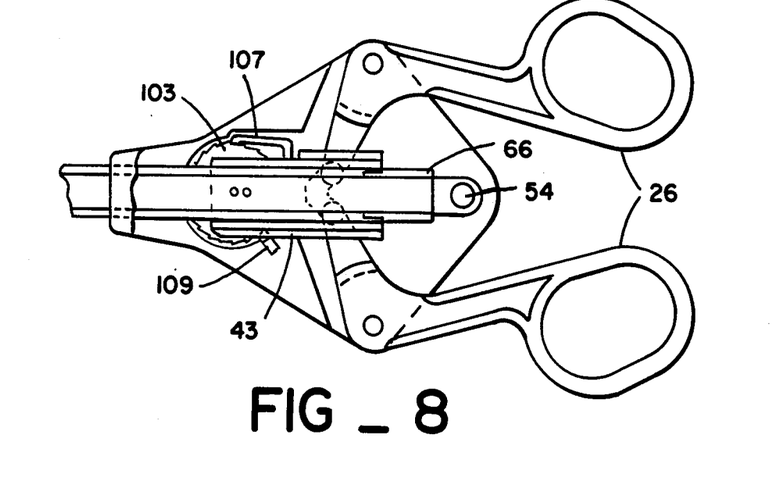
FIG. 8 is an enlarged plan view of the actuating mechanism within the housing of the tool, showing the handles and mechanism in the fully actuated position.
Figure 15:
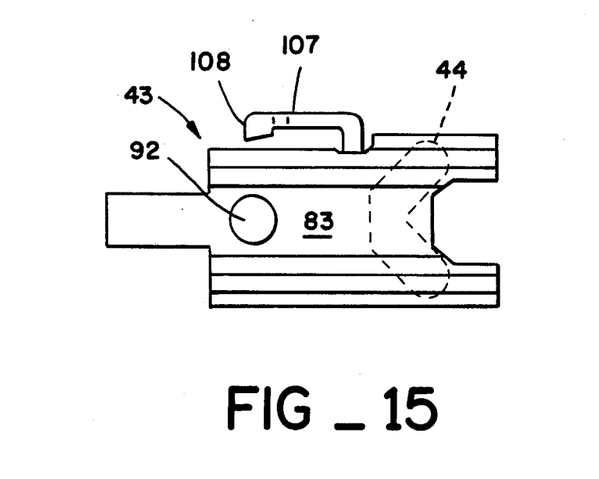
FIG. 15 is a plan view of the shuttle block of the tool.

As shown best in FIG. 15, the top surface of the shuttle block 43 is provided with a generally kidney-shaped recess 44 formed therein. The distal, interior ends of the dogleg portions 34 of the actuating levers include lugs 46 which are adapted to be received in sliding fashion in the recess 44. It should be noted that the shape of the recess 44 accommodates the arcuate paths of the lugs 46 as the levers are moved together, the lugs driving the block 43 to translate longitudinally and distally in the track, as shown in FIGS. 4 and 8. Likewise, outward movement of the levers causes the block 43 to translate proximally and return to the quiescent position of FIGS. 5 and 7.

Figure 10:
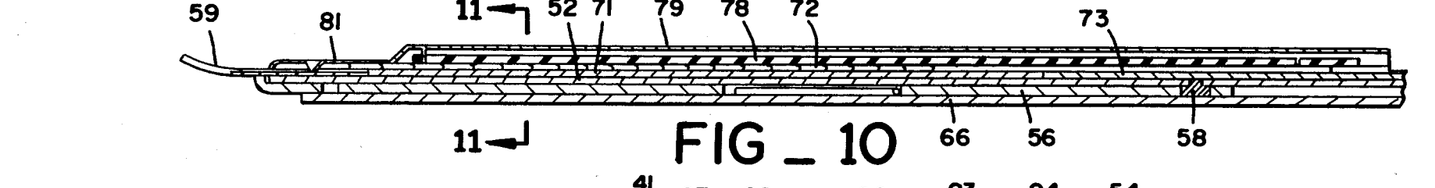
FIG. 10 is a cross-sectional side view of the longitudinally extending delivery and crimping mechanism of the tool.

The housing members also define a longitudinal passageway 51 extending through the distal end portion of the housing along the medial axis thereof. A jaw strut 52, comprising a planar, thin, elongated member, extends generally the entire length of the portion 22, through the passageway 51 and the entire length of the chamber 41, as shown in FIGS. 9 and 10. A hole 53 formed in the proximal end of the jaw strut (FIG. 13) receives therethrough an anchoring pin 54 disposed within the proximal end of the chamber 41, as shown in FIG. 9. Thus the jaw strut is fixedly secured to the housing portion 21. A pair of jaw members 56 extend longitudinally directly adjacent to the jaw strut, and include arcuate recesses 57 which receive a rivet 58 therebetween. The rivet is received in a hole 55 disposed in a medial portion of the jaw strut, thus joining the jaw members to the jaw strut in pivotting fashion about the member 58.

Figure 13:
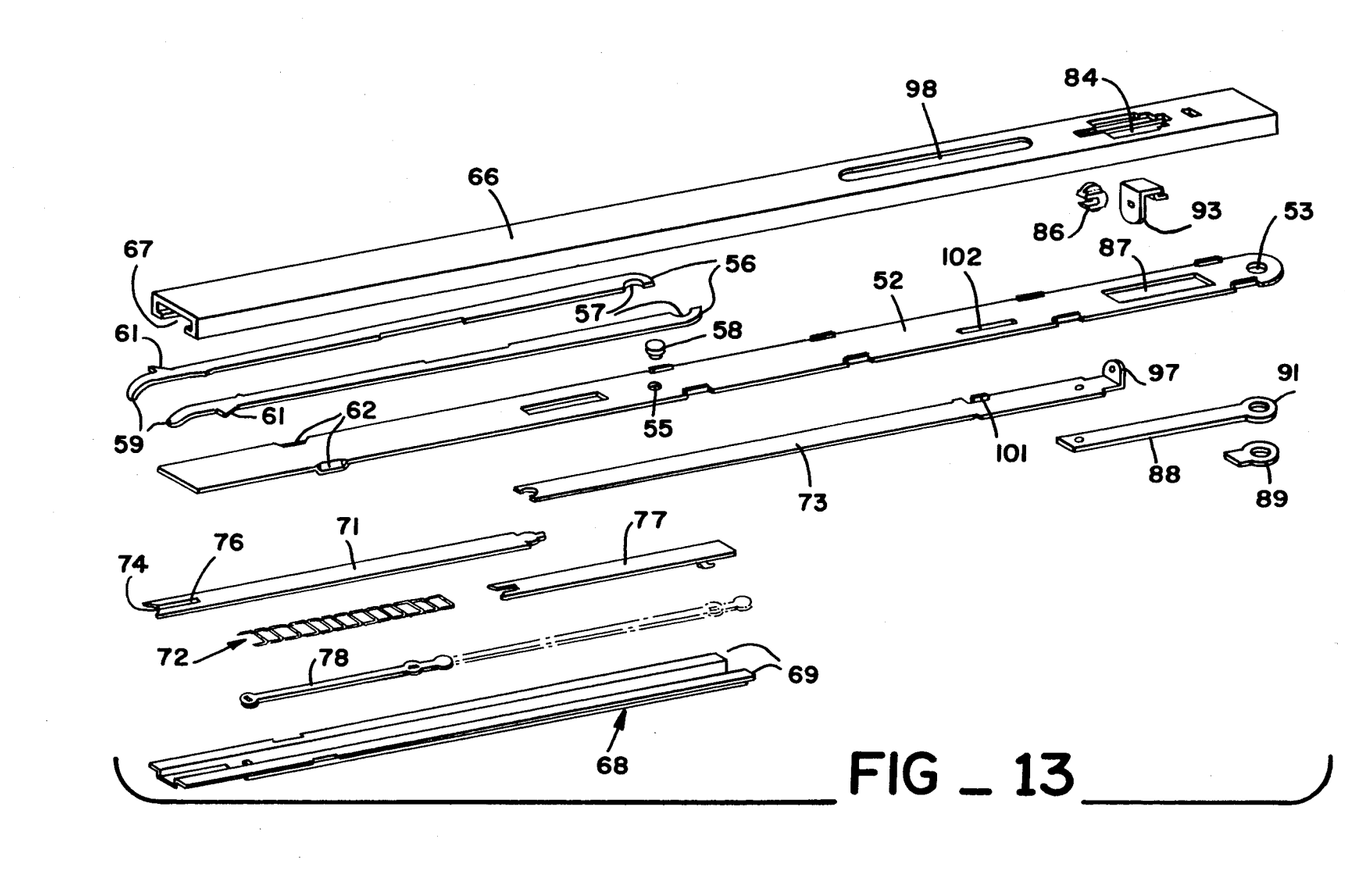
FIG. 13 is an exploded view of the components of the dispensing and crimping portion of the tool.
Figure 14:
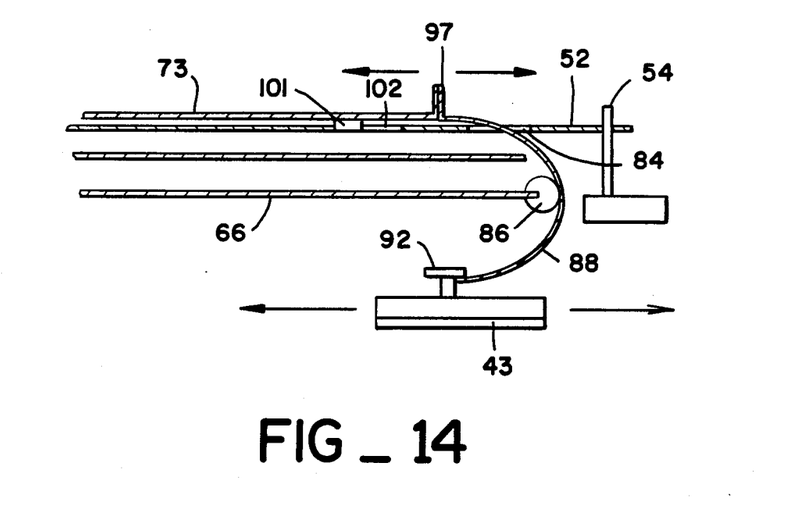
FIG. 14 is a schematic representation of the operation of the actuating mechanism of the tool of the present invention.

The distal end portions of the jaw members extend distally beyond the distal end of the strut, and are curved out of the plane of the stut, as shown in FIGS. 2 and 13. The laterally outwardly opposed sides of the distal portions of the jaw members include outwardly flaring camming surfaces 61, for purposes which will be described in the following. A leaf spring (not shown) extends between the jaw members to bias them resiliently each away from the other. The mutually confronting surfaces of the distal portions of the jaw members are provided with longitudinally extending grooves dimensioned to secure and retain the leg portions of a standard hemostatic clip in freely translating fashion.

A significant component of the portion 22 of the tool is a jaw housing member 66, shown most clearly in FIGS. 9–13. The jaw housing 66 comprises a channel-like member extending longitudinally from the interior of the housing 21, through the passageway 51, to the distal portion of the jaw members 56. It should be noted that the channel-like configuration of the member 66 provides substantial rigidity and stiffness to the portion 22. Indeed, the jaw strut 52 and the jaw members 56 are received within the channel cavity 67 of the member 66 (FIGS. 10 and 11), thereby supporting the jaw assembly, as well as other components to be described, without deviation from the longitudinal axis of the housing. It should also be noted that the jaw housing member is received in the housing 21 in longitudinally translatable fashion, as will be described.

Figure 11:
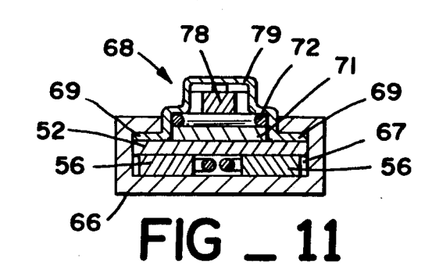
FIG. 11 is a cross-sectional end view taken along line 11—11 of FIG. 10.
Figure 12:
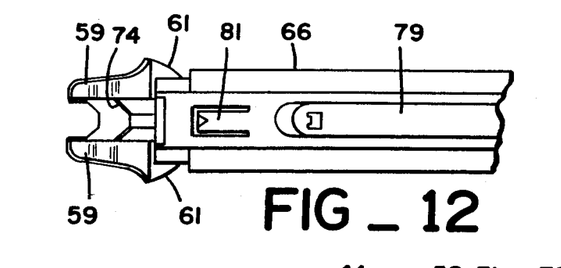
FIG. 12 is an enlarged plan view of the distal, jaw portion of the tool.

Also assembled to the jaw housing member 66 is a magazine housing member 68, shown in FIGS. 10–13. The member 68 is also channel-like in configuration, although shorter than the jaw housing, and includes opposed flanges 69 extending laterally outwardly and formed along the length thereof. The flanges 69 are received within the channel cavity 67, and are retained by the opposed side edges of the channel opening of the jaw housing 66. As shown in FIG. 11, the flanges 69, together with the jaw strut and the jaw members, substantially fill the channel cavity of the jaw housing and comprise a self-retaining assembly. Tabs 62 formed on the distal portion of the jaw strut 52 engage opposed notches in the outer edges of the magazine housing 66 to prevent longitudinal movement thereof.

The magazine housing 68 is provided with a stepped cross-sectional configuration, with a feeder slide 71 being translatably disposed within the wider portion thereof and impinging on one surface of the jaw strut. The feeder slide is a relatively short, flexible member which is joined to a feed drive member 73 extending through the channel cavity 67 into the housing 21. The distal end of the feeder slide 71 is adapted to be received and translate between the curved, distal ends 59 of the jaw members. The distal end of the feeder slide 71 is provided with a concave recess 74 configured to engage the web portion of the standard hemostatic clip.

Also within the wide portion of the magazine housing is a column 72 of hemostatic clips, arrayed in end-to-end, serial fashion, and translatably retained between the feeder slide 71 and the inner confines of the magazine housing for longitudinal movement only. A feed pusher 77 is disposed proximally of the column 72 and aligned therewith, and an elastic band 78 is disposed in the narrow step portion 79 of the magazine housing and linked under tension between the pusher 77 and a distal portion of the magazine housing. The tension of the band 78 urges the member 77 to push the column 72 distally toward the jaw member portions 59. An integrally formed leaf spring 81 urges the distal-most hermostatic clip of the column 72 out of column alignment and into a feed position aligned with the jaw members, thus dispensing a clip to the feed position whenever the feeder slide is fully retracted proximally to provide sufficient clearance for the dispensed clip. The distal detent tip of the spring 81 constricts the feed path of the dispensed clip, and retains the clip in the feed path. The feeder slide is then driven to engage the dispensed clip with the concave recess 74, and to drive the dispensed clip longitudinally past the tip of the spring 81 and between the open jaw members to the distal ends thereof, as will be described. A medial, longitudinal groove 76 extends proximally from the recess 74 to provide clearance for the distal tip of the spring 81 as the feeder slide translates past the spring 81.

Figure 16:
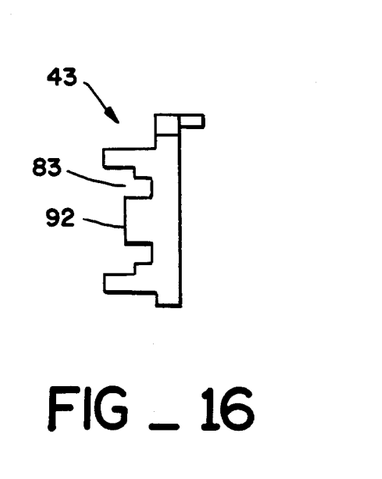
FIG. 16 is an end view of the shuttle block as shown in FIG. 15.

As shown in FIGS. 15 and 16, the shuttle block 43 includes a longitudinal passageway 83 which provides clearance for the jaw housing 66 and the feed drive member 73 and jaw strut 52 assembled therein to pass through the housing cavity 41 without interfering with the shuttle block. The proximal end of the jaw housing 66 includes an aperture 84 formed in the web portion thereof, and a pulley member 86 is joined fixedly to the distal edge of the aperture 84, as shown in FIGS. 9 and 13. The jaw strut 52 also includes an aperture 87 in the proximal end thereof generally adjacent to the aperture 84. A deformable, flexible band 88 includes one end 91 that extends through the aperture 87 of the jaw strut, through the aperture 84 of the jaw housing, and about the pulley member 86. The end 91 is joined to a reinforcing eyelet 89 and secured to a post 92 extending from the shuttle block. The other end of the flexible band 88 extends to be secured to the proximal end of the feed drive member 73.

Joined to the proximal edge of the aperture 84 is a spring bracket 93 extending orthogonally to the plane of the web of the jaw housing. A helical spring 94 is secured between the bracket 93 and the fixed post 54 of the housing 21. Another spring 96 is secured between the bracket 93 and a tab 97 extending from the proximal end of the feed drive member 73. The spring 96 has a relatively lower spring force constant than the spring 94. Furthermore, the spring 96 is adapted to be compressed during actuation of the mechanism, whereas the spring 94 is placed under tension during actuation.

The operation of the actuating mechanism may be understood with reference to FIGS. 7–9 and 14. In the quiescent position, the handle levers 26 diverge the maximum limit, the shuttle block 43 is disposed proximally in the housing 21, the feeder slide 71 is extended distally with the end portion thereof disposed between the jaw members, and a hemostatic clip is disposed between the portions 59 of the jaw members and positioned to be crimped and installed on a blood vessel. The handle levers are grasped and squeezed together, causing the dogleg portions thereof to drive the shuttle block 43 to begin to translate distally. The post 92 of the shuttle block translates freely in a slot 98 is the web of the jaw housing. The shuttle motion creates tension on the flexible band 88, pulling the band about the pulley 86 and causing proximal translation of the feed drive member 73. As a result the spring 96 undergoes compression between the tab 97 and the bracket 93. This motion continues until the distal end of the feeder slide 71 has cleared the jaw portions 59, and the jaws are thus free to be driven together to crimp the clip therebetween.

The proximal motion of the feed drive member 73 and the associated member 71 is limited by a tab 101 extending from the member 73 (FIG. 13) and received in a slot 102 formed in the fixed jaw strut 52. However, the further tension in the band 88 caused by further squeezing of the levers together creates a driving force on the pulley 86 which overcomes the resilient force of the spring 94. As a result, the pulley then acts to drive the jaw housing 66 to translate distally against the spring force 94. At the distal end of the jaw housing, the inner surfaces of the channel cavity 67 engage the camming surfaces 61 of the jaw members 56, urging the jaw members to rotate together and crimp completely the hemostatic clip disposed between the distal portions 59 thereof.

Upon release of the manual pressure on the levers 26, the tension of the spring 94 on the bracket 93 causes the jaw housing to retract proximally, and the jaws open again under the resilient urging of the leaf spring disposed therebetween. As noted above, full proximal retraction of the feeder slide provides clearance for the distal most clip in the magazine to be urged by the spring 81 into a feed position aligned with the jaws. The detent tip of the spring 81 retains the dispensed clip in this position during closure of the jaws and crimping of the clip held therein. When the jaws have opened fully, there is a clear feed path for the detained clip in the dispensed position.

As the spring 94 returns to the untensioned disposition, the compression of the spring 96 then drives the tab 97 to urge the feed drive member and the feeder slide distally. The end 74 then engages the newly dispensed clip and drives the clip distally as it translates, urging it past the detent tip of the spring 81 and placing the new clip at the distal end of the jaw portions 59. The new clip thus is positioned to be crimped and installed in the next cycle of operation. At the fully returned position, the shuttle block is again in its proximal location in the housing 21, and the levers are fully diverged, as shown in FIG. 7.

A further feature of the tool of the present invention is the provision of a counter display 27 which indicates the number of hemostatic clips remaining in the magazine assembly. The counter mechanism includes a disk-like wheel 103 having a continuous array of ratchet teeth 104 extending about the circumference thereof. The wheel 103 is received in a shallow recess 106 formed in the interior surface of the top member 31 of the housing 21. Extending from the one side of the shuttle block 43 is an arm 107 having a pawl 108 at the distal end thereof. When the shuttle is translated fully distally, at the point at which the clip in the jaws is fully crimped, the pawl 108 is driven to contact the periphery of the wheel 103 and engaging one of the ratchet teeth. The wheel is thus driven to rotate incrementally with each full actuation of the mechanism of the tool. Appropriate indicia 28 formed on the top surface of the wheel 103 are arranged to decrement by one unit with each incremental advance of the wheel, thus displaying the total number of clips remaining. A detent tab 109 engages the periphery of the wheel to prevent rotation of the wheel by any other means.

Thus it may be appreciated that the present invention provides a tool which employs relatively few components to achieve a complex though reliable actuation sequence. The shuttle block-flexible band mechanism operates and sequences properly both the feeder slide mechanism and the jaw housing, as well as the counter mechanism. The jaw housing provides lateral rigidity to the assembly 22, and also functions to operate the jaw members. This multiple functioning of components reduces the parts count and results in a tool which is inexpensive to manufacture. Thus the tool is adapted to be used once and discarded, a feature which is desirable in modern medical practice.

Further, it should be noted that the distance from the housing to the distal jaw portions 59 is fixed and invariable, so that accurate placement of the clip is not affected by actuating the levels. Also, the levers are linked together by their connection to the shuttle block, so that both levers must be converged an equal amount at all times during actuation. The result of this design feature is that the longitudinal axis of the tool always bisects the angle described by the handle levers, and the distal dispensing end is always at the same angular disposition with respect to the handles. This feature yields a superior "feel" to the tool, and alleviates any tendency to move the distal dispensing end from the desired placement position as the levers are actuated.

We claim:

1. A tool for storing, dispensing, and applying a plurality of hemostatic clips in serial fashion, comprising;
   magazine means for storing a plurality of hemostatic clips in column fashion;
   dispensing means for selectively removing and dispensing a hemostatic clip from one end of said column in serial, sequential fashion;
   jaw means for retaining and crimping a hemostatic clip;
   feed means for transferring a dispensed clip from said column to said jaw means,
   actuating means for operating said feed means, jaw means, and dispensing means in sequential interaction, including a flexible band coupled to said feed means, a pulley member about which said flexible band is passed, lever means for pulling said flexible band around said pulley member in such a direction to withdraw said feed means from said jaw means, a jaw housing extending from said actuating means and adapted for reciprocal translation to close and open said jaw means, means for joining said pulley member to one end of said jaw housing in force translating fashion, so that tension on said flexible band urges said jaw housing to extend from said tool, wherein said feed means includes a feeder slide assembly extending longitudinally from said tool in translatable fashion, and further including first spring means extending between said proximal end of said feeder slide assembly and said proximal end of said jaw housing and adapted to be compressed elastically therebetween.

2. The tool of claim 1, further including second spring means extending between said proximal end of said jaw housing and said tool housing and adapted to be elongated elastically therebetween.

3. The tool of claim 2, wherein manual convergence of said handle levers drives said shuttle block longitudinally and initially pulls said flexible band about said pulley member to retract said feeder slide assembly proximally and to compress said first spring means, thereafter the tension in said flexible band urges said pulley member to drive said jaw housing to translate distally to close said jaw members.

4. A tool for storing, dispensing, and applying a plurality of hemostatic clips in serial fashion, comprising;
   magazine means for storing a plurality of hemostatic clips in column fashion;
   dispensing means for selectively removing and dispensing a hemostatic clip from one end of said column in serial, sequential fashion;
   jaw means for retaining and crimping a hemostatic clip;
   feed means for transferring a dispensed clip from said column to said jaw means,
   actuating means for operating said feed means, jaw means, and dispensing means in sequential interaction, including a flexible band coupled to said feed means, a pulley member about which said flexible band is passed, lever means for pulling said flexible band around said pulley member in such a direction to withdraw said feed means from said jaw means, further including a jaw housing extending from said actuating means and adapted for reciprocal translation to close and open said jaw means, means for joining said pulley member to one end of said jaw housing in force translating fashion, so that tension on said flexible band urges said jaw housing to extend from said tool, said actuating means including means connected to said feed means and said jaw housing so that tension applied to said flexible band first pulls said band about said pulley member and withdraws said feed means fully from said jaw means, then drives said pulley member and said jaw housing to extend from said tool, and release of tension on said flexible band retracts said jaw housing and then releases said band about said pulley member to extend said feed means.

5. The tool of claim 4, wherein said means connected to said feed means and said jaw housing includes a shuttle block disposed in said tool and adapted for reciprocal translation therein, said flexible band being connected at one end to said shuttle block, and at the opposed end to said feed means.

6. The tool of claim 4, wherein said feed means is disposed within said jaw housing for parallel translation along a generally common axis.

7. The tool of claim 4, further including first spring means for maintaining resilient expansion force applied between said jaw housing and said feed means to urge said feed means to extend and urge said jaw housing to retract.

8. The tool of claim 7, further including second spring means extending between said jaw housing and said tool and disposed to resiliently oppose extension of said jaw housing.

9. A tool for storing, dispensing, and applying a plurality of hemostatic clips in serial fashion, comprising;
   magazine means for storing a plurality of hemostatic clips in column fashion;
   dispensing means for selectively removing and dispensing a hemostatic clip from one end of said column in serial, sequential fashion;
   jaw means for retaining and crimping a hemostatic clip;
   feed means for transferring a dispensed clip from said column to said jaw means,
   actuating means for operating said feed means, jaw means, and dispensing means in sequential interaction, including a flexible band coupled at one end to said feed means, a non-rotating pulley member about which said flexible band is passed, a shuttle block coupled to the other end of said flexible band, said shuttle block being disposed for reciprocal translation to drive said flexible band about said pulley member, and lever means for driving said shuttle block reciprocally and pulling said flexible band around said pulley member in such a direction to withdraw said feed means from said jaw means.

10. A tool for storing, dispensing, and applying a plurality of hemostatic clips in serial fashion, comprising;
   magazine means for storing a plurality of hemostatic clips in column fashion;
   dispensing means for selectively removing and dispensing a hemostatic clip from one end of said column in serial, sequential fashion;
   jaw means for retaining and crimping a hemostatic clip;
   feed means for transferring a dispensed clip from said column to said jaw means,
   actuating means for operating said feed means, jaw means, and dispensing means in sequential interaction, including a flexible band coupled to said feed means, a non-rotating, linearly translatable pulley member about which said flexible band is passed, and lever means for pulling said flexible band around said pulley member in such a direction to withdraw said feed means from said jaw means.

11. A tool for storing, dispensing, and applying a plurality of hemostatic clips in serial fashion, comprising;
   magazine means for storing a plurality of hemostatic clips in column fashion;
   dispensing means for selectively removing and dispensing a hemostatic clip from one of said column in serial, sequential fashion;
   jaw means for retaining and crimping a hemostatic clip;
   jaw closing means;
   feed means for transferring a dispensed clip from said column to said jaw means,
   actuating means for operating said feed means, jaw means, and dispensing means in sequential interaction, including a flexible band coupled to said feed means, a pulley member about which said flexible band is passed, said pulley member being operably connected to said jaw closing means, and lever means for pulling said flexible band around said pulley member in such a direction to withdraw said feed means from said jaw means and to translate said pulley member to actuate said jaw closing means.

12. The tool of claim 11, wherein said lever means includes a shuttle block disposed for reciprocal translation within said tool, said flexible band being connected to said shuttle block.

13. The tool of claim 12, wherein said lever means includes a pair of handle levers pivotally secured to said tool and disposed to be squeezed closed and released open to drive said shuttle block in a reciprocal path.

14. The tool of claim 11, wherein said jaw closing means includes a jaw housing extending from said actuating means, said jaw housing including portions adapted for reciprocal translation about said jaw means to close and open said jaw means, means for joining said pulley member to one end of said jaw housing in force translating fashion, so that tension on said flexible band urges said jaw housing to extend from said tool.

15. The tool of claim 14, wherein said feed means includes a feeder slide assembly extending longitudinally from said tool in translatable fashion.

16. The tool of claim 15, wherein said feeder slide assembly is received within said channel cavity of said jaw housing.

17. The tool of claim 16, wherein said jaw means includes a pair of jaw members, and said feeder slide assembly includes a distal end portion adapted to be received between said jaw members in the fully open position.

18. The tool of claim 17, wherein said distal end portion of said feeder slide assembly includes an end surface adapted to engage the hemostatic clip in said feed position and to translate the hemostatic clip therefrom to the distal end of said jaw members.

19. The tool of claim 11, wherein said jaw means includes a jaw strut extending distally from said housing generally along said longitudinal axis, said jaw strut being fixedly secured to said housing.

20. The tool of claim 19, further including a pair of laterally opposed jaw members secured to a distal portion of said jaw strut in limited rotational fashion.

21. The tool of claim 20, wherein said jaw members include mutually confronting surfaces, and a groove extending generally longitudinally in each of said confronting surfaces and dimensioned to retain and secure a leg portion of a hemostatic clip in slidable fashion.

22. The tool of claim 21, wherein said jaw members further include flared camming surfaces extending longitudinally along laterally opposed edge portions thereof.

23. The tool of claim 22, further including a jaw housing extending longitudinally from said housing and generally parallel to said jaw strut.

24. The tool of claim 23, wherein said jaw housing comprises an elongated, channel-like member having a channel cavity extending therein, said jaw strut being received within and extending through said channel cavity.

* * * * *